United States Patent
Okuya

(10) Patent No.: US 12,303,267 B2
(45) Date of Patent: May 20, 2025

(54) PSYCHOLOGICAL CONDITION ESTIMATION SYSTEM, PSYCHOLOGICAL CONDITION ESTIMATION METHOD, PROGRAM, AND METHOD FOR GENERATING ESTIMATION MODEL

(71) Applicant: Panasonic Intellectual Property Management Co., Ltd., Osaka (JP)

(72) Inventor: Teruhisa Okuya, Osaka (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 847 days.

(21) Appl. No.: 17/440,887

(22) PCT Filed: Mar. 6, 2020

(86) PCT No.: PCT/JP2020/009737
§ 371 (c)(1),
(2) Date: Sep. 20, 2021

(87) PCT Pub. No.: WO2020/203051
PCT Pub. Date: Oct. 8, 2020

(65) Prior Publication Data
US 2022/0160275 A1    May 26, 2022

(30) Foreign Application Priority Data
Mar. 29, 2019  (JP) ................. 2019-069215

(51) Int. Cl.
*A61B 5/16*      (2006.01)
*A61B 5/378*     (2021.01)
(Continued)

(52) U.S. Cl.
CPC .............. *A61B 5/165* (2013.01); *A61B 5/378* (2021.01); *A61B 5/38* (2021.01); *A61B 5/381* (2021.01); *A61B 5/383* (2021.01); *G16H 40/63* (2018.01)

(58) Field of Classification Search
CPC .................... A61B 5/16; A61B 10/00
(Continued)

(56) References Cited

U.S. PATENT DOCUMENTS 5,884,626 A    3/1999  Kuroda
6,129,681 A    10/2000 Kuroda
(Continued)

FOREIGN PATENT DOCUMENTS

JP    H08-117199 A     5/1996
JP    2003-290179 A    10/2003
(Continued)

OTHER PUBLICATIONS

International Search Report for corresponding Application No. PCT/JP2020/009737, mailed Apr. 21, 2020.
(Continued)

*Primary Examiner* — Kurt Fernstrom
(74) *Attorney, Agent, or Firm* — Renner, Otto, Boisselle & Sklar, LLP

(57) ABSTRACT

A psychological condition estimation system includes an acquisition unit and an estimation unit. The acquisition unit acquires information about respective activity levels of a plurality of sensory areas of a subject's brain. The estimation unit estimates a sense, which is highly related to the subject's psychological condition, out of a plurality of types of senses corresponding respectively to the plurality of sensory areas, based on the information, acquired by the acquisition unit, about the activity levels of the plurality of sensory areas when the subject is exposed to multiple types of stimuli.

9 Claims, 8 Drawing Sheets

(51) Int. Cl.
  *A61B 5/38*    (2021.01)
  *A61B 5/381*   (2021.01)
  *A61B 5/383*   (2021.01)
  *G16H 40/63*   (2018.01)

(58) Field of Classification Search
  USPC .......................................................... 434/236
  See application file for complete search history.

(56) References Cited

U.S. PATENT DOCUMENTS

| | | | | |
|---|---|---|---|---|
| 6,625,485 | B2* | 9/2003 | Levendowski | A61B 5/7207 |
| | | | | 128/920 |
| 7,574,254 | B2* | 8/2009 | Milgramm | A61B 5/377 |
| | | | | 600/300 |
| 8,239,015 | B2* | 8/2012 | Morikawa | A61B 5/7264 |
| | | | | 600/545 |
| 8,265,743 | B2* | 9/2012 | Aguilar | A61B 5/38 |
| | | | | 600/544 |
| 8,392,250 | B2* | 3/2013 | Pradeep | G06Q 30/0244 |
| | | | | 705/14.41 |
| 8,823,792 | B2* | 9/2014 | Omi | G08B 21/06 |
| | | | | 340/576 |
| 9,292,858 | B2* | 3/2016 | Marci | A61B 5/16 |
| 9,451,303 | B2* | 9/2016 | Kothuri | G06Q 30/0201 |
| 10,604,160 | B2* | 3/2020 | Matsumura | G06F 3/013 |
| 2006/0025698 | A1 | 2/2006 | Nakagawa | |
| 2010/0145215 | A1* | 6/2010 | Pradeep | A61B 5/377 |
| | | | | 600/546 |
| 2011/0245624 | A1* | 10/2011 | Ballegaard | A61B 5/4035 |
| | | | | 600/300 |
| 2012/0130196 | A1* | 5/2012 | Jain | A61B 5/45 |
| | | | | 600/300 |
| 2015/0029087 | A1 | 1/2015 | Klappert | |
| 2015/0033245 | A1 | 1/2015 | Klappert | |
| 2015/0033258 | A1 | 1/2015 | Klappert | |
| 2015/0033259 | A1 | 1/2015 | Klappert | |
| 2015/0033262 | A1 | 1/2015 | Klappert | |
| 2015/0033266 | A1 | 1/2015 | Klappert | |
| 2016/0012747 | A1* | 1/2016 | Garrues Remirez | A61B 5/168 |
| | | | | 434/236 |
| 2016/0366462 | A1 | 12/2016 | Klappert | |
| 2019/0247662 | A1* | 8/2019 | Poltroak | A61N 1/36025 |
| 2020/0008725 | A1* | 1/2020 | Bach | A61B 5/16 |
| 2020/0222010 | A1* | 7/2020 | Howard | G06N 5/02 |

FOREIGN PATENT DOCUMENTS

| | | |
|---|---|---|
| JP | 2006-034803 A | 2/2006 |
| JP | 2010-264038 A | 11/2010 |
| JP | 2013-027570 A | 2/2013 |
| JP | 2016-532360 A | 10/2016 |
| WO | 2015/013045 A1 | 1/2015 |
| WO | 2018/030018 A1 | 2/2018 |

OTHER PUBLICATIONS

Written Opinion for corresponding Application No. PCT/JP2020/009737, mailed Apr. 21, 2020.

Ando Hiroshi, "Human Multisensory Information Processing and Psychophysical and Brain Activity Analysis Techniques" May 26, 2008 The Institute of Image Information and Television Engineers, ITE Technical Report vol. 32, No. 21, pp. 13-14, with partial English translation.

* cited by examiner

PSYCHOLOGICAL CONDITION ESTIMATION SYSTEM, PSYCHOLOGICAL CONDITION ESTIMATION METHOD, PROGRAM, AND METHOD FOR GENERATING ESTIMATION MODEL

TECHNICAL FIELD

The present disclosure generally relates to psychological condition estimation systems, psychological condition estimation methods, programs, and methods for generating estimation model. More particularly, the present disclosure relates to a psychological condition estimation system, a psychological condition estimation method, and a program, to be used for estimating a constituent factor of a subject's psychological condition, and a method for generating an estimation model which may be used in the psychological condition estimation system.

BACKGROUND ART

A biometric information display device is disclosed in Patent Literature 1.

The biometric information display device of Patent Literature 1 includes a biometric information detection means, a detection result display means, and an area display means.

The biometric information display means detects at least two types of biometric information based on a pulse wave signal and an electrocardiographic signal of a subject. The detection result display means displays, along with a past detection result, the two types of biometric information detected by the biometric information detection means by plotting the two types of biometric information at corresponding points on a two-dimensional coordinate system set on a display screen. The area display means displays, on the display screen, a plurality of areas showing correspondence between the points on the two-dimensional coordinate system and the subject's conditions by superimposing those areas on the detection result by the detection result display means.

CITATION LIST

Patent Literature

Patent Literature 1: JP 2006-34803 A

SUMMARY OF INVENTION

The biometric information display device of Patent Literature 1 may display a change in a subject's (target person's) psychological condition in real time. However, the device provides the user with no information about a constituent factor relevant to the change in the psychological condition.

It is therefore an object of the present disclosure to provide a psychological condition estimation system, a psychological condition estimation method, and a program, which may be useful for determining a constituent factor of a subject's psychological condition, and also provide a method for generating an estimation model which may be used in the psychological condition estimation system.

A psychological condition estimation system according to an aspect of the present disclosure includes an acquisition unit and an estimation unit. The acquisition unit acquires information about respective activity levels of a plurality of sensory areas of a subject's brain. The estimation unit estimates a sense, which is highly related to the subject's psychological condition, out of a plurality of types of senses corresponding respectively to the plurality of sensory areas, based on the information, acquired by the acquisition unit, about the activity levels of the plurality of sensory areas when the subject is exposed to multiple types of stimuli.

A psychological condition estimation method according to another aspect of the present disclosure includes an acquisition step and an estimation step. The acquisition step includes acquiring information about respective activity levels of a plurality of sensory areas of a subject's brain. The estimation step includes estimating a sense, which is highly related to the subject's psychological condition, out of a plurality of types of senses corresponding respectively to the plurality of sensory areas, based on the information about the activity levels of the plurality of sensory areas as acquired when the subject is exposed to multiple types of stimuli.

A program according to still another aspect of the present disclosure is designed to cause one or more processors to perform the psychological condition estimation method described above.

A method for generating an estimation model according to yet another aspect of the present disclosure is a method for generating an estimation model for use in the estimation unit of the psychological condition estimation system described above. The method for generating an estimation model includes an acquisition step and a model generating step. The acquisition step includes acquiring, when a subject is exposed to multiple types of stimuli, information about respective activity levels of a plurality of sensory areas of the subject's brain. The model generating step includes generating the estimation model based on input data and output data by machine learning using, as the input data, information about respective activity levels of the plurality of sensory areas, and also using, as the output data, the sense highly related to the subject's psychological condition.

DESCRIPTION OF EMBODIMENTS

(1) First Embodiment

(1.1) Overview

Figure 1:
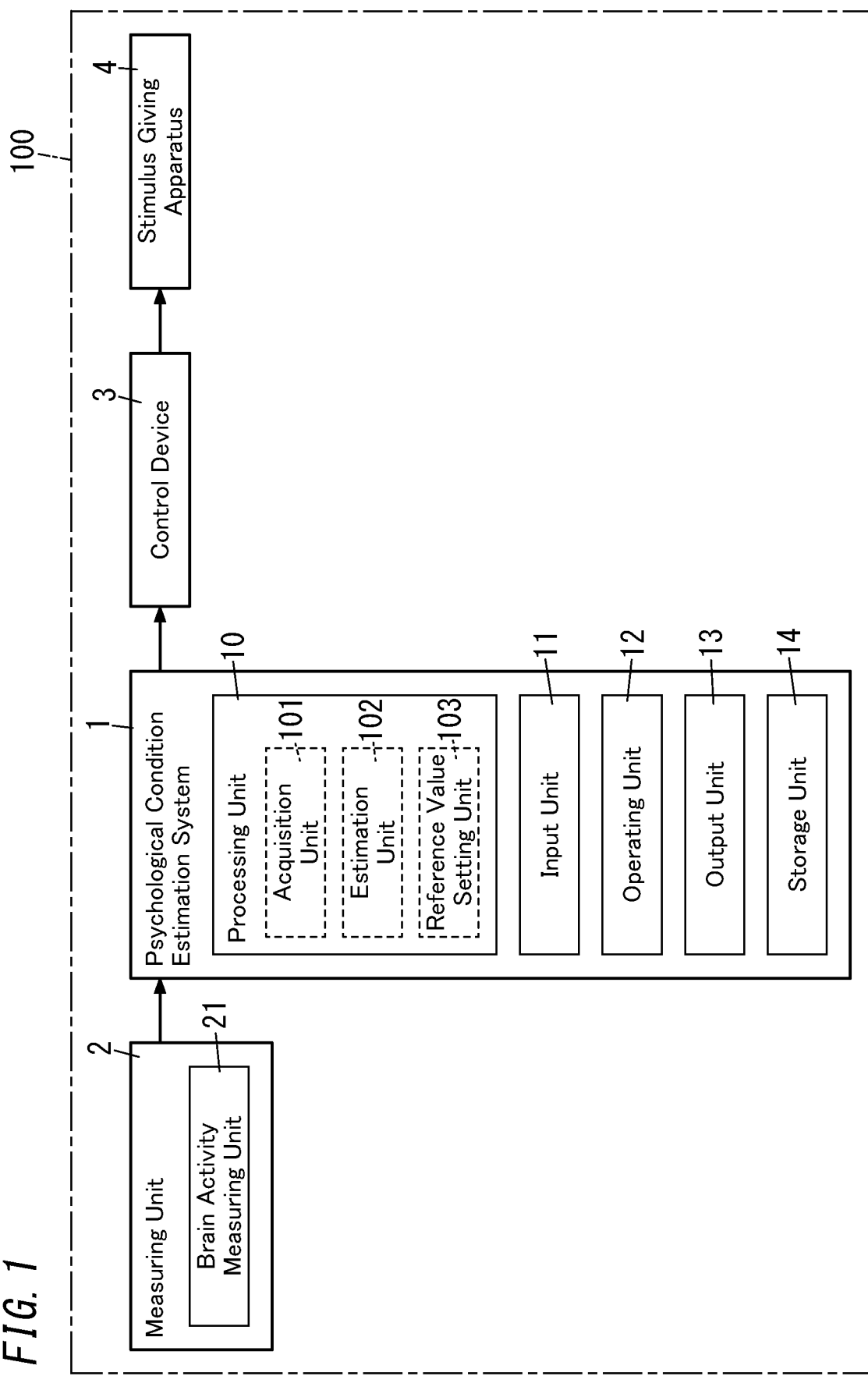
FIG. 1 is a block diagram of a control system including a psychological condition estimation system according to a first embodiment.

FIG. 1 shows a block diagram of a control system 100 which includes a psychological condition estimation system 1 according to an exemplary embodiment.

As shown in FIG. 1, the psychological condition estimation system 1 according to this embodiment includes an acquisition unit 101 and an estimation unit 102. The acquisition unit 101 acquires information about respective activity levels of a plurality of sensory areas 91-95 of a subject's brain 90 (see FIG. 2). When the subject is exposed to multiple types of stimuli, the estimation unit 102 estimates, based on the information, acquired by the acquisition unit 101, about the activity levels of the plurality of sensory areas 91-95, a sense, which is highly related to the subject's psychological condition, out of a plurality of types of senses corresponding respectively to the plurality of sensory areas 91-95.

The psychological condition estimation system 1 according to this embodiment estimates, based on the information about the activity levels of the plurality of sensory areas 91-95, the sense to be highly related to the subject's psychological condition out of a plurality of types of senses. Therefore, the psychological condition estimation system 1 may be useful for determining a constituent factor of the subject's psychological condition.

(1.2) Details (1.2.1) Configuration

The control system 100 including the psychological condition estimation system 1 of this embodiment will be described in further detail with reference to the drawings.

The control system 100 includes a measuring unit 2, a control device 3, and a stimulus giving apparatus 4, in addition to the psychological condition estimation system 1.

The measuring unit 2 measures the subject's biometric information. The measuring unit 2, for example, is a wearable terminal that the subject may put on his or her body.

The measuring unit 2 includes a brain activity measuring unit 21 for measuring the activity level of the subject's brain 90. The brain activity measuring unit 21 noninvasively measures the activity levels of the plurality of areas of the subject's brain 90 when placed in position on his or her head, for example. In this embodiment, the brain activity measuring unit 21 is implemented as an NIRS (Near Infra-Red Spectroscopy) encephalometer using the NIRS technique.

The NIRS encephalometer captures an image of a cerebral cortex area of the brain 90 by, for example, irradiating the subject with a near infrared ray having a wavelength of around 800 nm from over his or her scalp and measuring the transmitted light. It is known that the concentration of hemoglobin increases in an activated area (i.e., an area with a high activity level) of the brain 90. Moreover, the near infrared ray having a wavelength of approximately 800 nm for use in the NIRS encephalometer passes through a human body tissue such as scalp and skull but is absorbed into hemoglobin in the blood. Therefore, the activity level in each area of the brain 90 may be measured by observing, for example, the intensity variation of the transmitted near infrared ray and an increase or decrease in the concentration of hemoglobin in the brain 90 image captured by the NIRS encephalometer.

The measuring unit 2 outputs the measurement result to the psychological condition estimation system 1 by wired or wireless communication.

The psychological condition estimation system 1 includes a processing unit 10, an input unit 11, an operating unit 12, an output unit 13, and a storage unit 14.

The input unit 11 is a communications interface for communicating with the measuring unit 2 via cables or wirelessly. The input unit 11 receives the measurement result from the (brain activity measuring unit 21 of the) measuring unit 2.

The processing unit 10 includes the acquisition unit 101, the estimation unit 102, and a reference value setting unit 103. The processing unit 10 is implemented as, for example, a microcomputer including a processor and a memory. The computer system performs the function of the processing unit 10 by making the processor execute an appropriate program. In other words, the functions of the processing unit 10 (including the acquisition unit 101, the estimation unit 102, and the reference value setting unit 103) are implemented as the computer system including the processor and the memory. The program may be stored in advance in the memory or may also be downloaded via a telecommunications line such as the Internet or distributed after having been stored in a non-transitory storage medium such as a memory card.

The acquisition unit 101 of the processing unit 10 acquires, based on the measurement results received from the brain activity measuring unit 21, information about respective activity levels of a plurality of sensory areas of the subject's brain 90. In this embodiment, the acquisition unit 101 of the processing unit 10 acquires information about respective activity levels of a plurality of primary sensory areas in the cerebral cortex of the subject's brain 90.

Figure 2:
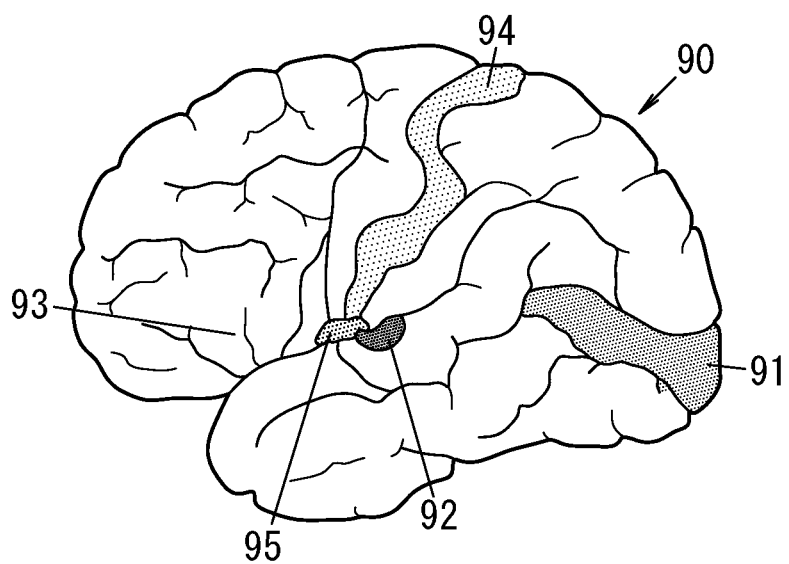
FIG. 2 illustrates a subject's brain.

As shown in FIG. 2, the cerebral cortex of the brain 90 includes the plurality of sensory areas (primary sensory areas) 91-95. The plurality of sensory areas (primary sensory areas) include a visual area 91, an auditory area 92, an olfactory area 93, a somatosensory area 94, and a gustatory area 95. The visual area 91 is an area of the cerebral cortex associated with a visual sense and located in the occipital lobe. The auditory area 92 is an area of the cerebral cortex associated with an auditory sense and located in the temporal lobe. The olfactory area 93 is an area of the cerebral cortex associated with an olfactory sense and located in the frontal lobe. The somatosensory area 94 is an area of the cerebral cortex associated with a somatic sensation and located in the parietal lobe. The gustatory area 95 is an area of the cerebral cortex associated with a gustatory sense and located between the somatosensory area and the olfactory area.

The acquisition unit 101 acquires, based on the measurement result received from the measuring unit 2 (the brain 90 image), information about activity levels of respective sensory areas (namely, visual area 91, auditory area 92, olfactory area 93, somatosensory area 94, and gustatory area 95) associated with the five senses.

The activity levels of the sensory areas 91-95 of the subject's brain 90 depend on how much the subject's attention is directed to a stimulus to which the subject is exposed. The control system 100 includes a stimulus giving apparatus 4 as an apparatus which may give stimulus to the subject. For example, the stimulus giving apparatus 4 may give the subject multiple types of stimuli corresponding respectively to multiple types of senses.

The stimulus giving apparatus 4 may include, for example, a lighting device, a display device, and the like, as a device which may give stimulus to the subject's visual sense, for example. The lighting device, for example, may adjust brightness, light color, color temperature, and luminance. The display device may display an appropriate image on its monitor.

The stimulus giving apparatus 4 may include a sound emitter, for example, as a device which may give a stimulus to the subject's auditory sense, for example. The sound emitter includes a loudspeaker, from which appropriate voice, music, or environmental sound may be output, for example.

The stimulus giving apparatus 4 may include an odor generator, for example, as a device which may give a stimulus to the subject's olfactory sense, for example. The odor generator is, for example, an aroma diffuser which may generate a chemical that is a source of an appropriate odor (smell) to be sensed by the olfactory sense.

The stimulus giving apparatus 4 may include a blower, an air conditioner and the like, for example, as a device which may give a stimulus to the subject's somatic sensation, for example. The blower and the air conditioner, for example, may adjust direction and volume of airflow.

The stimulus giving apparatus 4 may include a taste stimulator, for example, as a device which may give a stimulus to the subject's gustatory sense, for example. The taste stimulator, for example, may stimulate the subject's gustatory sense by having an electrode put on the subject's tongue (tastebud) and letting an electric current flow through the electrode.

The operation of the stimulus giving apparatus 4 may be controlled by the control device 3. The control system 100 may include, other than the stimulus giving apparatus 4, a device which may reduce the stimulus to the subject such as an air purifier which may reduce the olfactory stimulus by removing chemical within a space.

In this embodiment, the processing unit 10 has a first mode and a second mode, as its operation modes. The operation mode of the processing unit 10 may be switched in response to, for example, the input operation performed on the operating unit 12. The operating unit 12 may have, for example, a push button for switching the operation mode of the processing unit 10.

The first mode is a mode in which the reference value setting unit 103 of the processing unit 10 operates. The first mode is performed in, for example, a state where the subject is not exposed to any stimulus from the stimulus giving apparatus 4. The first mode may be performed in, for example, a state where the subject is not exposed to a peculiar stimulus. The state in which the subject is not exposed to a peculiar stimulus may be a state in which the subject is exposed to a reference stimulus. The state in which the subject is not exposed to a peculiar stimulus may be, for example, a state in which the time it takes for the subject to adapt to the environment of a room 200 has passed since a point in time when the subject entered the room 200 with the control system 100 installed. The state in which the subject is not exposed to a peculiar stimulus is similar to a state in which the subject is taking a rest at his or her house in daily life, for example, and may be a state in which the subject is relaxed, for example. In the first mode, based on the information acquired by the acquisition unit 101 about the activity levels of the plurality of sensory areas 91-95, the processing unit 10 sets a plurality of reference values which are respectively to be used as bases (baselines) for the activity levels of the plurality of sensory areas 91-95. The plurality of reference values have one-to-one correspondence to the activity levels of the plurality of sensory areas 91-95.

In the first mode, the (reference value setting unit 103 of the) processing unit 10 obtains, with respect to each of the plurality of sensory areas 91-95, a measure of central tendency of the activity levels acquired by the acquisition unit 101 while operating in the first mode. The reference value setting unit 103 obtains, with respect to each of the plurality of sensory areas 91-95, an average value of the activity levels in the sensory area, as the measure of central tendency of the activity levels. The reference value setting unit 103 sets the obtained measure of central tendency (in this embodiment, the average value) of the activity levels as a reference value. However, the reference value is not limited to this, but the reference value setting unit 103 may obtain a minimum, median, or maximum value of the activity levels of the corresponding sensory area, as the measure of central tendency of the activity levels.

Specifically, the reference value setting unit 103 sets a plurality of reference values with respect to the respective activity levels of the plurality of sensory areas 91-95 (namely, the visual area 91, auditory area 92, olfactory area 93, somatosensory area 94, and gustatory area 95). That is to say, the reference value setting unit 103 sets a visual area reference value, an auditory area reference value, an olfactory area reference value, a somatosensory area reference value, and a gustatory area reference value with respect to the activity level of the visual area 91, the activity level of the auditory area 92, the activity level of the olfactory area 93, the activity level of the somatosensory area 94, and the activity level of the gustatory area 95, respectively.

The reference value setting unit 103 has the plurality of reference values thus set stored in the storage unit (reference value storage unit) 14. In other words, the plurality of reference values having one-to-one correspondence to the activity levels of the plurality of sensory areas 91-95 are stored in the storage unit (reference value storage unit) 14.

The storage unit 14 is a semiconductor memory such as a RAM (Random Access Memory) or an EEPROM (Electrically Erasable Programmable Read Only Memory). Note that the storage unit 14 is not limited to such a semiconductor memory, but may also be a hard disk drive, for example.

The second mode is a mode in which the estimation unit 102 of the processing unit 10 operates. The second mode may be performed in, for example, a state where the subject is exposed to at least one type of stimulus from the stimulus giving apparatus 4. In the second mode, based on the information acquired by the acquisition unit 101 about the activity levels of the plurality of sensory areas 91-95, the processing unit 10 estimates the sense, which is highly related to the subject's psychological condition, out of a plurality of types of senses corresponding respectively to the plurality of sensory areas 91-95.

In the second mode, the (estimation unit 102 of the) processing unit 10 obtains an attention level with respect to each of the plurality of sensory areas 91-95. The attention level is a level indicating how much the subject is paying attention to stimuli to the a plurality of types of senses corresponding respectively to the plurality of sensory areas 91-95. In this embodiment, the attention level is defined as the difference between the activity level acquired by the acquisition unit 101 while the processing unit 10 is operating in the second mode and the reference value stored in the reference value storage unit 14.

The estimation unit 102 obtains a plurality of attention levels with respect to the plurality of sensory areas 91-95, i.e., a plurality of attention levels with respect to the plurality of types of stimuli, respectively. The estimation unit 102 obtains an attention level in response to a visual stimulus (hereinafter referred to as a "visual area attention level"), an attention level in response to an auditory stimulus (hereinafter referred to as an "auditory area attention level"), an attention level in response to an olfactory stimulus (hereinafter referred to as an "olfactory area attention level"), an attention level in response to a somatosensory stimulus (hereinafter referred to as a "somatosensory area attention level"), and an attention level in response to a gustatory stimulus (hereinafter referred to as a "gustatory area attention level").

The attention level with respect to each sensory areas corresponds to the difference between the measure of central tendency of the activity levels acquired by the acquisition unit 101 while the processing unit 10 is operating in the first mode and the activity level acquired by the acquisition unit 101 while the processing unit 10 is operating in the second mode. Therefore, having a high attention level with respect to a sensory area means that this sensory area is activated more significantly than when the reference value has been obtained, i.e., the subject's attention is directed to a stimulus with respect to this sensory area.

Figure 3:
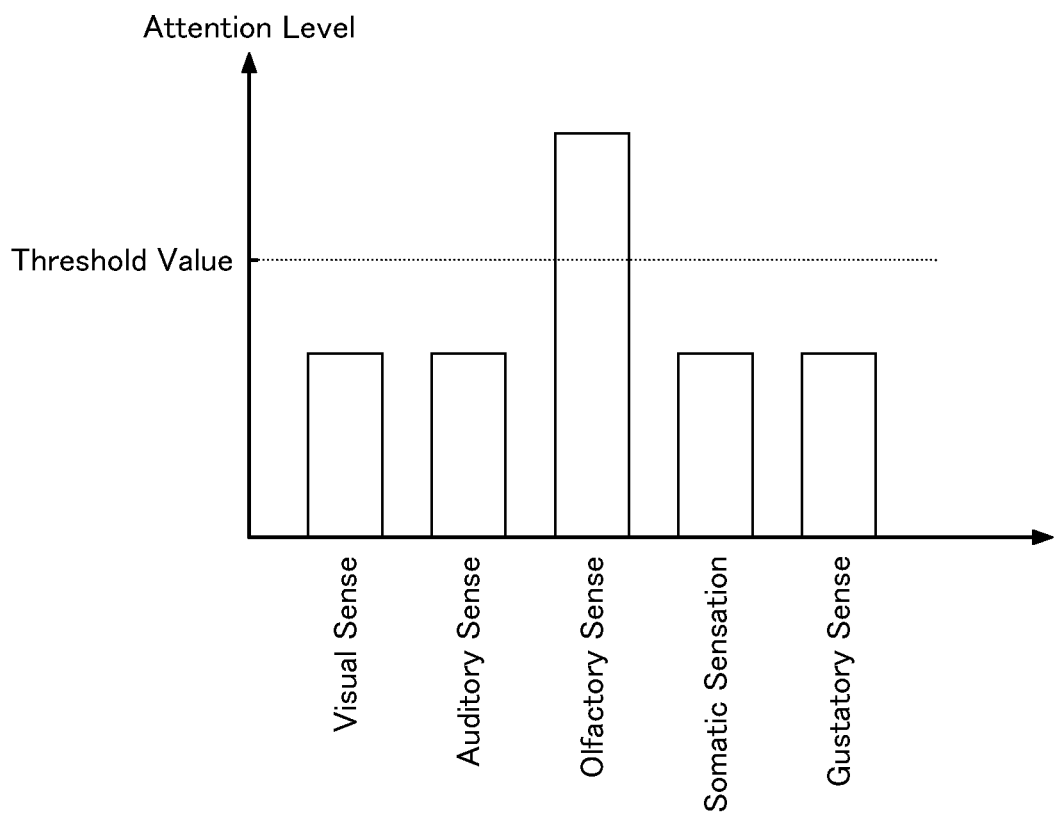
FIG. 3 is a graph showing attention levels of a plurality of sensory areas corresponding to a plurality of types of senses.

The estimation unit 102 estimates a sense with the highest attention level, out of a plurality of types of senses corresponding respectively to the plurality of sensory areas 91-95, to be the sense highly related to the subject's psychological condition. For example, as shown in FIG. 3, if the attention level with respect to the olfactory sense (i.e., the olfactory area attention level) is the highest among the visual sense, the auditory sense, the olfactory sense, the somatic sensation, and the gustatory sense, the estimation unit 102 estimates that among the five types of senses (five senses), the olfactory sense will be highly related to the subject's psychological condition. The subject's psychological condition may be represented by the subject's emotion, for example. Examples of the subject's emotions include astonishment, excitedness, pleasure, happiness, elatedness, tenseness, nervousness, anger, frustration, displeasure, sadness, depression, boredom, fatigue, contentedness, comfortableness, sereness, and relaxedness. For example, if the attention level with respect to the olfactory sense is the highest in a state where the subject is "displeased" condition, the estimation unit 102 may estimate that the subject's olfactory sense (stimulus to the subject's olfactory sense) is highly likely causing his or her displeased emotion.

The output unit 13 is a communications interface for communicating with the control device 3 via cables or wirelessly. The psychological condition estimation system 1 outputs the estimation results acquired by the estimation unit 102 to the control device 3 via the output unit 13. Moreover, the psychological condition estimation system 1 outputs the respective attention levels with respect to the plurality of sensory areas 91-95 to the control device 3 via the output unit 13.

The control device 3 controls the stimulus giving apparatus 4, based on the estimation result and the attention levels with respect to the plurality of sensory areas 91-95 provided by the output unit 13 of the psychological condition estimation system 1. The control device 3 controls the stimulus giving apparatus 4 to, for example, change or maintain the attention level of the sense, which is estimated by the psychological condition estimation system 1 to be highly related to the subject's psychological condition. Specifically, the control device 3 may control the stimulus giving apparatus 4 to increase or decrease the attention level of the sense that is estimated by the psychological condition estimation system 1 to be highly related to the subject's psychological condition.

(1.2.2) Exemplary Use

An exemplary use of the control system 100 according to this embodiment will be described.

In this exemplary use, suppose a situation in which the user of the control system 100 as the subject wants to reduce the chances of having his or her attention disturbed by a stimulus from the environment as much as possible by use of the control system 100, for the purpose of focusing on something such as work.

Figure 4:
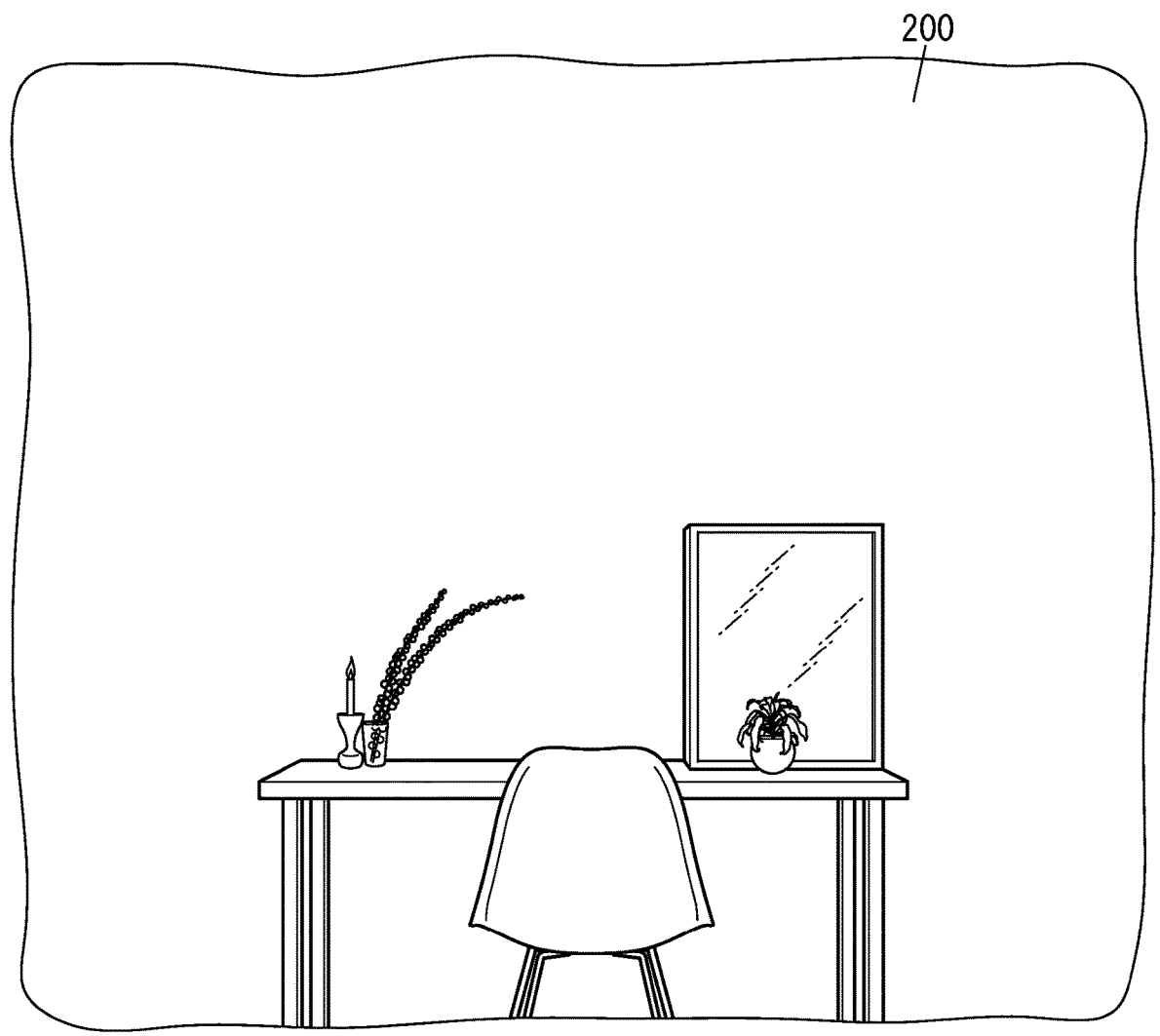
FIG. 4 shows an example of a room used when a reference value is set in the psychological condition estimation system according to the first embodiment.

First, the user makes the control system 100 operate in the first mode and has the reference value(s) stored in the storage unit (reference value storage unit) 14 in advance. The reference value(s) is/are set under a situation in which the subject is not exposed to a peculiar stimulus. For example, as shown in FIG. 4, in a room 200 where the control system 100 is installed, the lighting device, included in the stimulus giving apparatus 4, is lighted in daylight color, while the sound emitter and the odor generator, which are also included in the stimulus giving apparatus 4, are kept OFF. In this situation, the activity levels of the sensory areas 91-95 of the user's brain 90 are measured by using the control system 100 and based on the activity levels thus measured, reference values are set. In other words, the reference value setting unit 103 of the psychological condition estimation system 1 sets the reference values based on the activity levels of the plurality of sensory areas 91-95 as acquired by the acquisition unit 101 when the subject is not exposed to any stimulus.

Next, in the room 200 where the control system 100 is installed, the user performs something such as work while making the psychological condition estimation system 1 of the control system 100 operate in the second mode. The psychological condition estimation system 1 obtains the respective activity and attention levels with respect to the sensory areas 91-95 of the brain 90 based on the information acquired from the measuring unit 2.

In this situation, suppose, for example, that the highest attention level with respect to any one of the plurality of sensory areas 91-95 has exceeded a predetermined threshold value (e.g., see the graph of "olfactory sense" in FIG. 3). This means that the user's attention is directed to a stimulus (odor) corresponding to this sensory area (olfactory area 93). This stimulus (odor) may be a stimulus, to which the subject is inevitably exposed in the room 200 (environment), for example. That is to say, the psychological condition estimation system 1 estimates that the user's (current) attention is (excessively) directed to the olfactory stimulus since the attention level with respect to the olfactory area 93 has exceeded the predetermined threshold value. In this case, the estimation unit 102 estimates the olfactory sense to be the sense highly related to the subject's psychological condition.

Thus, the control device 3 removes the chemical within the air as a source of the odor by activating the air purifier, for example, to prevent the subject from getting disturbed by the odor. Alternatively, the control device 3 may have an appropriate odor (e.g., odor such as a rose or lavender odor for relaxing the subject) generated by the odor generator, to prevent the subject from getting disturbed by the odor.

Similarly, for example, if the attention level with respect to the visual area 91 exceeds the predetermined threshold value (if the user's attention is directed to the information collected through his or her eyes), the estimation unit 102 estimates the visual sense to be the sense highly related to the subject's psychological condition. The control device 3 may change, for example, the quantity of light, light color, luminance, and color temperature of the lighting device, which is included in the stimulus giving apparatus 4.

As described above, the psychological condition estimation system 1 according to this embodiment may estimate the stimulus, to which the subject's attention is directed (i.e., the sense highly related to the subject's current psychological condition). This allows the psychological condition estimation system 1 to be useful for determining the constituent factor of the subject's psychological condition.

Furthermore, the control system 100 including the psychological condition estimation system 1 according to this embodiment may also stimulate the sense estimated by the psychological condition estimation system 1 to be highly related to the subject's current psychological condition. Therefore, if the subject's psychological condition is represented by his or her emotion, for example, the sense highly related to the subject's current psychological condition may be stimulated for the subject, so that the subject's emotion changes to a more positive emotion (e.g., to change a "displeased" condition into a "relaxed" condition).

(2) Second Embodiment (2.1) Configuration

Figure 5:
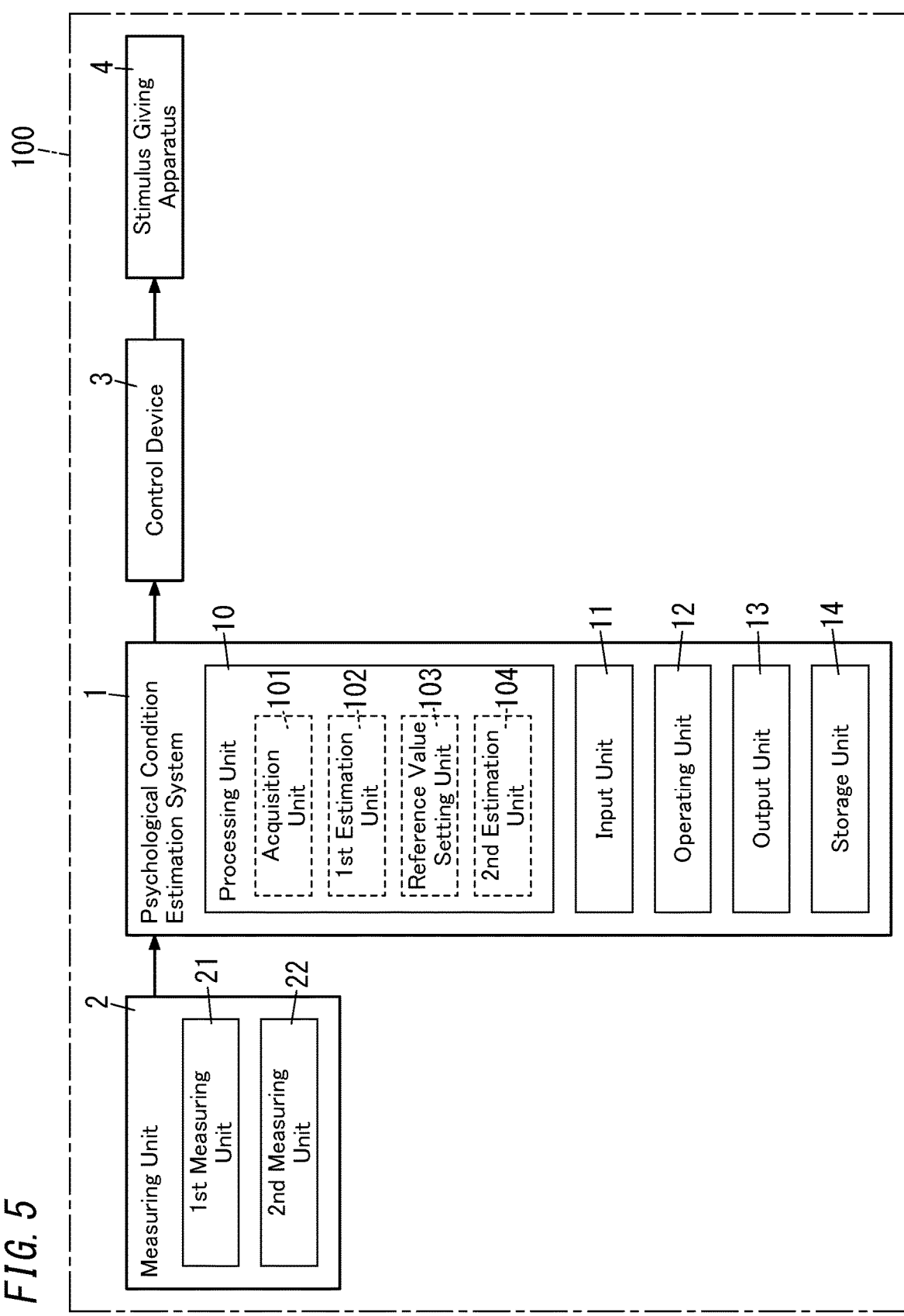
FIG. 5 is a block diagram of a control system including a psychological condition estimation system according to a second embodiment.

FIG. 5 shows a block diagram of a control system 100 which includes a psychological condition estimation system 1 according to a second embodiment. In the following description, any constituent element of the control system 100 according to this second embodiment, having the same function as a counterpart of the control system 100 of the first embodiment described above, will be designated by the same reference numeral as that counterpart's, and description thereof will be omitted as appropriate herein.

A measuring unit 2 according to this embodiment further includes a second measuring unit 22, in addition to a first measuring unit 21 which corresponds to the brain activity measuring unit 21. The first measuring unit 21 measures a physiological reaction of a subject's central nervous system by measuring the activity level of the subject's brain 90. On the other hand, the second measuring unit 22 measures a physiological reaction of the subject's autonomic nervous system. The second measuring unit 22 measures various parameters indicating the subject's conditions of health such as heart rate, blood pressure, respiration rate, skin temperature, and electrodermal activity (electrodermal activity level), for example.

Moreover, the psychological condition estimation system 1 of this embodiment further includes a second estimation unit 104, in addition to a first estimation unit 102 which corresponds to the estimation unit 102 of the first embodiment.

The second estimation unit 104 estimates, based on the measurement results obtained by the first measuring unit 21 and the second measuring unit 22, the subject's psychological condition by using the subject's level of valence (hereinafter also referred to as a "valence level") and his or her level of arousal (hereinafter also referred to as an "arousal level") as indices. The subject's psychological condition is represented by his or her emotion, for example.

Figure 6:
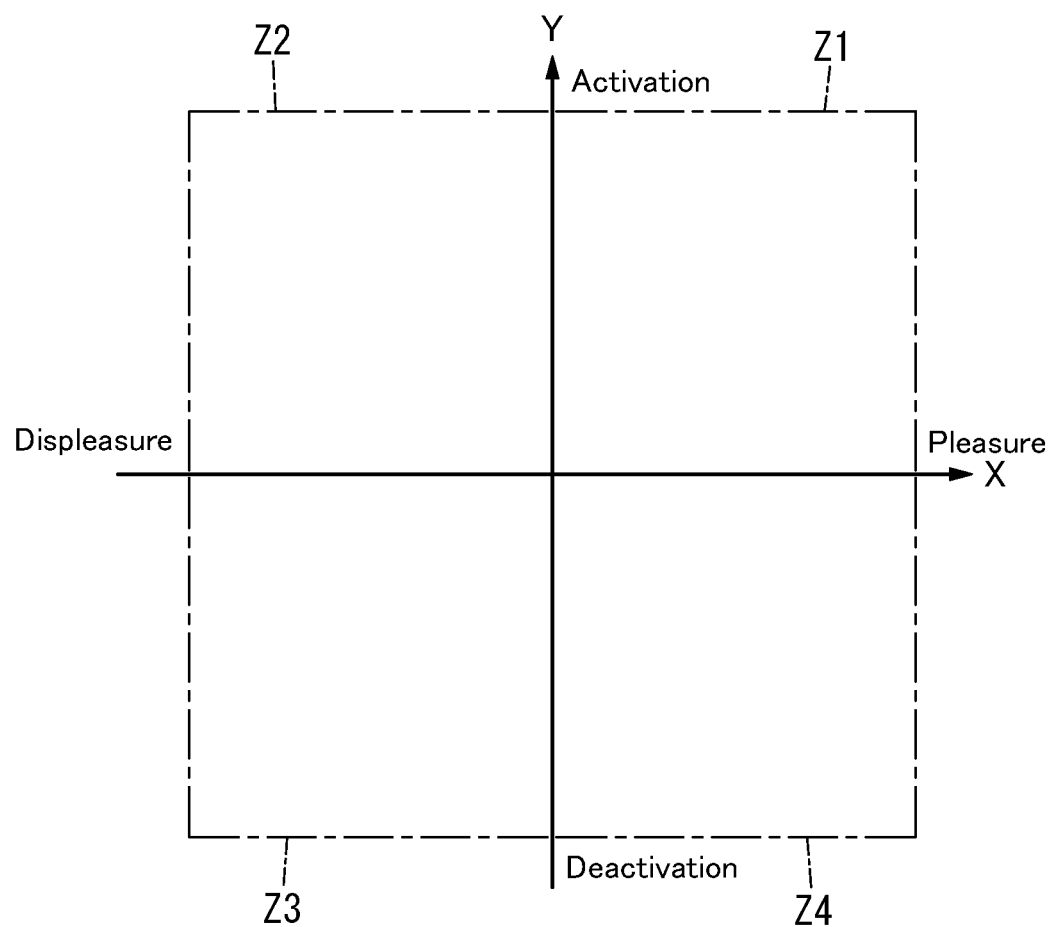
FIG. 6 is a chart showing a two-dimensional psychological model which uses a level of valence and a level of arousal as indices.

The valence level is an index indicating a level of the subject's pleasure. The arousal level is an index indicating a level of his or her arousal. As shown in FIG. 6, the psychological condition may be represented by, for example, a two-dimensional psychological model (e.g., Russell's circumplex model) which uses the valence level and the arousal level as indices. In this two-dimensional psychological model, the X-axis indicates the valence level, and the Y-axis indicates the arousal level.

The valence level on the X-axis has a positive domain and a negative domain, which represent "pleasure" and "displeasure," respectively. Regarding the valence level, the degree of pleasure increases as the level (absolute value) thereof increases in the positive domain of the X-axis, while the degree of displeasure increases (i.e., the degree of pleasure decreases) as the level (absolute value) thereof increases in the negative domain of the X-axis.

The arousal level on the Y-axis has a positive domain and a negative domain, which represent "activation" and "deactivation", respectively. Regarding the arousal level, the degree of activation increases as the level (absolute value) thereof increases in the positive domain of the Y-axis, while the degree of deactivation increases (i.e., the degree of activation decreases) as the level (absolute value) thereof increases in the negative domain of the Y-axis.

The psychological condition has its types classified, depending on in which of the four quadrants a coordinate position, determined by a combination of the valence level and the arousal level, is located in the two-dimensional coordinate system of the two-dimensional psychological model. A first quadrant Z1 is associated with what is called a "refreshed" condition. If the coordinate position is located within the first quadrant Z1, this means that the psychological condition may be astonishment, excitedness, pleasure, happiness, or elatedness, for example. A second quadrant Z2 is associated with what is called an "frustrated" condition. If the coordinate position is located within the second quadrant Z2, this means that the psychological condition may be tenseness, nervousness, anger, frustration, or displeasure, for example. A third quadrant Z3 is associated with what is called a "bored" condition. If the coordinate position is located within the third quadrant Z3, this means that the psychological condition may be sadness, depression, boredom, or fatigue, for example. A fourth quadrant Z4 is associated with what is called a "relaxed" condition. If the coordinate position is located within the fourth quadrant Z4, this means that the psychological condition may be contentedness, comfortableness, sereness, or relaxedness, for example.

The second estimation unit 104 estimates the subject's psychological condition by obtaining the valence level and the arousal level based on the measurement results by the (first measuring unit 21 and the second measuring unit 22 of the) measuring unit 2. The second estimation unit 104 estimates the subject's psychological condition by determining the coordinate position representing the subject's psychological condition within the two-dimensional coordinate system of the two-dimensional psychological model.

A processing unit 10 outputs the estimations results obtained by the first estimation unit 102 and the second estimation unit 104 to a control device 3 via an output unit 13.

The control device 3 controls the stimulus giving apparatus 4, based on the estimation results and the attention levels with respect to the plurality of sensory areas 91-95 provided by the output unit 13 of the psychological condition estimation system 1. The control device 3 controls, if the subject's current psychological condition estimated by the second estimation unit 104 is not his or her desired condition, for example, the stimulus giving apparatus 4 to change the subject's psychological condition to his or her desired condition. In this case, the control device 3 estimates that a constituent factor of the subject's current psychological condition will be a stimulus to the sense estimated by the first estimation unit 102 to be highly related to the subject's psychological condition. Thus, the control device 3 controls the stimulus giving apparatus 4 so as to change the stimulus to the sense.

(2.2) Exemplary Use

Figure 7:
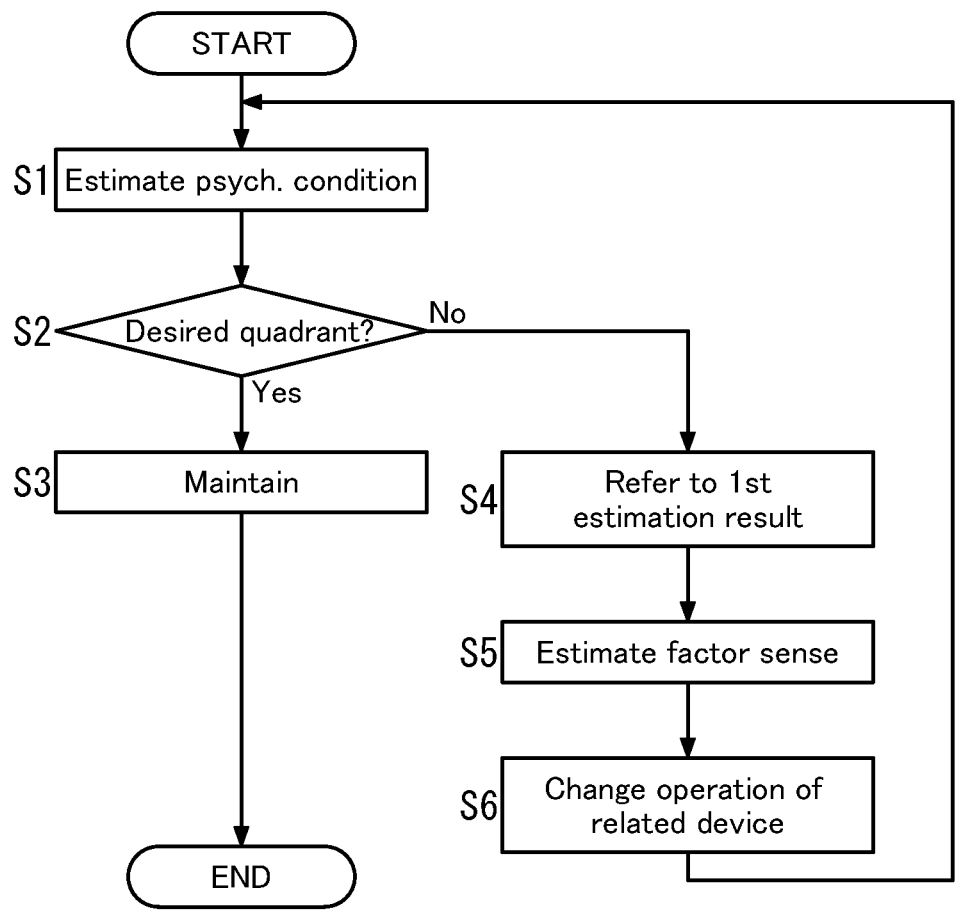
FIG. 7 is a flow chart showing an operation of the control system including the psychological condition estimation system according to the second embodiment.

An exemplary use of the control system 100 according to this embodiment will be described with reference to a flow chart of FIG. 7.

In this exemplary use, suppose a particular situation where the user as the subject uses the control system 100 for the purpose of relaxation.

As in the first embodiment, the user makes the control system 100 operate in the first mode in advance and has reference values stored in the storage unit (reference value storage unit) 14.

Next, the user makes the control system 100 operate and inputs his or her desired psychological condition (a desired psychological condition which he or she wants to achieve) by operating the operating unit 12. In this embodiment, a relaxed condition is input as a desired psychological condition because the user wants to be relaxed.

The control system 100 lights the lighting device, which is included in a stimulus giving apparatus 4, so that the lighting device emits light in a lightbulb color to reproduce the atmosphere of what is called a bar or a lounge, in order to relax the user. Moreover, the control system 100 generates a rose odor, which is generally considered to have a relaxation effect, from an aroma diffuser included in the stimulus giving apparatus 4.

The second estimation unit 104 of the psychological condition estimation system 1 estimates the user's psychological condition, based on the measurement results obtained by the measuring unit 2 (in S1). The psychological condition estimation system 1 outputs the estimation result to the control device 3. The control device 3 determines whether or not the estimation result obtained by the second estimation unit 104 falls within a quadrant (which is one of the first quadrant Z1 to fourth quadrant Z4) corresponding to the desired psychological condition according to the two-dimensional psychological model (in S2). In this case, the control device 3 determines whether or not the estimation result obtained by the second estimation unit 104 (second estimation result) falls within the fourth quadrant Z4 which corresponds to the relaxed condition.

If the estimation result obtained by the second estimation unit 104 falls within the quadrant corresponding to the desired psychological condition according to the two-dimensional psychological model (if the answer is YES in S2), the control device 3 decides that the user is in his or her desired psychological condition and maintains the stimulus giving apparatus 4 in the current state.

If the estimation result obtained by the second estimation unit 104 does not fall within the quadrant corresponding to the desired psychological condition according to the two-dimensional psychological model (if the answer is NO in S2), the control device 3 refers to the estimation result obtained by the first estimation unit 102 (first estimation result) (in S4) and acquires information about a sense which is highly related to the user's psychological condition, out of a plurality of types of senses (five senses). Then, the control device 3 determines, based on the estimation results obtained by the first estimation unit 102 and the second estimation unit 104, a constituent factor which prevents the user's psychological condition from turning into his or her desired condition. Specifically, the control device 3 estimates that the sense which is estimated by the first estimation unit 102 to be highly related to the user's psychological condition is the constituent factor (factor sense) preventing the user's psychological condition from turning into his or her desired condition (in S5). For example, as shown in FIG. 3, if the estimation result obtained by the second estimation unit 104 reveals that the attention level with respect to the olfactory sense is the highest among the five types of senses, the control device 3 estimates that an odor is the constituent factor preventing the user's psychological condition from turning into his or her desired condition.

Then, the control device 3 changes the operation mode of a particular device that would give a stimulus to the sense estimated by the first estimation unit 102 (hereinafter referred to as a "related device") included in the stimulus giving apparatus 4 (in S6). For example, the user may dislike a rose odor. Therefore, the control device 3 either deactivates the aroma diffuser, which is included in the stimulus giving apparatus 4 or makes the aroma diffuser emit a different odor such as a lavender odor, instead of the rose odor.

After changing the operation mode of the stimulus giving apparatus 4, the control device 3 estimates the user's psychological condition by acquiring the estimation result from the second estimation unit 104 (in S1) and determines whether or not the user's psychological condition has turned into his or her desired condition (relaxed condition) (in S2). The control device 3 repeats the above described processing until the user's psychological condition turns into his or her desired condition.

As described above, in the psychological condition estimation system 1 according to this embodiment, the subject's psychological condition (in this embodiment, the subject's emotion) is estimated by the second estimation unit 104, and the sense highly related to the subject's psychological condition is estimated by the first estimation unit 102. This allows the subject's current psychological condition and the sense that is the constituent factor causing this psychological condition, to be estimated in combination.

The control system 100 may induce the subject's psychological condition into his or her desired condition by using the estimation results obtained by the first estimation unit 102 and the second estimation unit 104 in combination.

Note that the control device 3 may refer to the estimation result obtained by the first estimation unit 102 (first estimation result) even if the estimation result obtained by the second estimation unit 104 falls within the quadrant corresponding to the desired psychological condition according to the two-dimensional psychological model (if the answer is YES in S2). Optionally, the control device 3 may control the operation of the stimulus giving apparatus 4 so that the apparatus that may give a stimulus to the sense highly related to the user's psychological condition operates so as to turn the user's psychological condition into his or her more desirable condition (e.g., to increase the degree of pleasure if the coordinate position representing the psychological condition is located within the fourth quadrant Z4).

(3) Method for Generating Estimation Model

Figure 8:
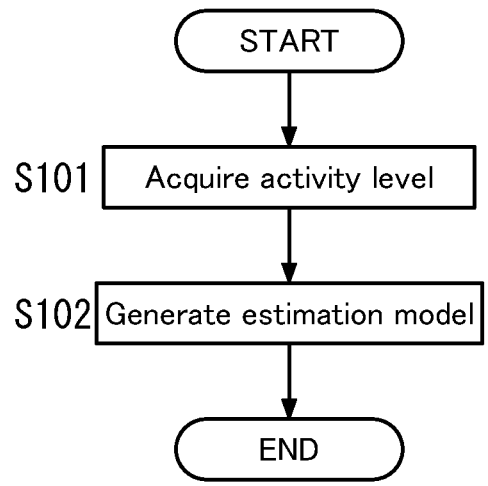
FIG. 8 is a flow chart showing a method for generating an estimation model.

An estimation model used in the estimation unit 102 (first estimation unit) of the psychological condition estimation system 1 may be generated by the method for generating an estimation model shown in FIG. 8. Specifically, the method for generating an estimation model according to one aspect of the present disclosure includes an acquisition step (S101) and a model generating step (S102). The acquisition step includes acquiring information about respective activity levels of a plurality of sensory areas (at least two of the above sensory areas 91-95) of the subject's brain 90, when the subject is exposed to multiple types of stimuli. The model generating step includes generating an estimation model based on input data and output data by machine learning using, as the input data, information about respective activity levels of a plurality of sensory areas (at least two of the above sensory areas 91-95), and also using, as the output data, the sense highly related to the subject's psychological condition.

(4) Variations

Note that the embodiment described above is only an exemplary one of various embodiments of the present disclosure and should not be construed as limiting. Rather, the exemplary embodiment may be readily modified in various manners depending on a design choice or any other factor without departing from the scope of the present disclosure. The variations to be described below may be adopted in combination as appropriate. The functions of the psychological condition estimation system 1 may also be implemented as, for example, a psychological condition estimation method, a (computer) program, or a non-transitory storage medium that stores the program.

A psychological condition estimation method according to an aspect includes an acquisition step and an estimation step. The acquisition step includes acquiring information about respective activity levels of a plurality of sensory areas 91-95 of a subject's brain 90. The estimation step includes estimating a sense, which is highly related to the subject's psychological condition, out of a plurality of types of senses corresponding respectively to the plurality of sensory areas 91-95, based on the information about the activity levels of the plurality of sensory areas 91-95 as acquired when the subject is exposed to a plurality of types of stimuli.

A program according to another aspect is designed to cause one or more processors to perform the psychological condition estimation method described above.

The psychological condition estimation system 1 according to the present disclosure includes a computer system in its processing unit 10, for example. The computer system may include, as principal hardware components, a processor and a memory. The functions of the psychological condition estimation system 1 according to the present disclosure may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be implemented as a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits include a system LSI, a very large-scale integrated circuit (VLSI), and an ultra-large scale integrated circuit (VLSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be integrated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

Also, in the embodiment described above, the plurality of constituent elements (or the functions) of the psychological condition estimation system 1 are integrated together in a single housing. However, this is not an essential configuration for the psychological condition estimation system 1. Alternatively, those constituent elements (or functions) of the psychological condition estimation system 1 may be distributed in multiple different housings. Alternatively, at least some functions of the psychological condition estimation system 1 may be implemented as, for example, a server device and a cloud computing system as well.

The psychological condition estimation system 1 may be used only with the measuring unit 2. That is to say, the information about the sense which is estimated by the psychological condition estimation system 1 to be highly related to the subject's psychological condition may be used for a purpose other than controlling the stimulus giving apparatus 4 using the control device 3. For example, by collecting information, from a plurality of persons, about the sense highly related to the subject's psychological condition by using the psychological condition estimation system 1, a sense having significant influence on the psychological condition of the plurality of persons, among the plurality of senses, may be estimated.

Options of the a plurality of types of senses which are estimated by the psychological condition estimation system 1 to be highly related to the subject's psychological condition do not have to be all of the five senses. In other words, the plurality of types of senses may include at least two senses selected from the group consisting of the five senses (namely, visual sense, auditory sense, olfactory sense, somatic sensation, and gustatory sense). The a plurality of types of senses preferably include at least the visual sense, the auditory sense, and the olfactory sense.

The multiple types of stimuli may be a number of types of stimuli corresponding respectively to multiple different ones of the plurality of sensory areas 91-95. For example, when the subject is exposed to the multiple types of stimuli corresponding respectively to multiple different ones of the plurality of sensory areas 91-95, the estimation unit 102 may estimate, based on the information, acquired by the acquisition unit 101, about the activity levels of the plurality of sensory areas, the sense highly related to the subject's psychological condition out of the plurality of types of senses corresponding respectively to the plurality of sensory areas 91-95.

For example, as described in the "(1.2.2) Exemplary use" section, the multiple types of stimuli that the subject is exposed to may include a stimulus, to which the subject is inevitably exposed from the environment. That is to say, the estimation unit 102 may estimate the sense highly related to the subject's psychological condition, out of the plurality of types of senses corresponding respectively to the plurality of sensory areas 91-95, based on the information, acquired by the acquisition unit 101, about the activity levels of the plurality of sensory areas 91-95 when the subject is exposed to the multiple types of stimuli from the environment other than the stimulus giving apparatus 4.

For example, as described in the "(2.2) Exemplary use" section, if the subject is exposed to the multiple types of stimuli applied by the stimulus giving apparatus 4, the estimation unit 102 may estimate, based on the information, acquired by the acquisition unit 101, about the activity levels of the plurality of sensory areas 91-95, the sense highly related to the subject's psychological condition, out of the plurality of types of senses corresponding respectively to the plurality of sensory areas 91-95.

In short, a situation "when the subject is exposed to the multiple types of stimuli" may refer to a situation in which the subject is not intentionally exposed to any stimulus from the stimulus giving apparatus 4 (when the subject is exposed to multiple types of stimuli from only the environment). Naturally, the situation "when the subject is exposed to the multiple types of stimuli" may be the situation when the subject is (intentionally) exposed to the multiple types of stimuli from the stimulus giving apparatus 4, for example.

The subject's psychological condition is not limited to his or her emotion, but may also be, for example, the sense of incompatibility or compatibility that the subject feels toward the environment.

The sensory area(s), from which information about the activity level(s) is acquired by the acquisition unit 101, is/are not limited to the primary sensory area(s). The sensory area(s), from which information about the activity level(s) is acquired by the acquisition unit 101, may include higher-order sensory areas such as secondary sensory area(s) or tertiary sensory area(s), in addition to, or instead of, the primary sensory area(s).

The acquisition unit 101 may acquire the information about the activity levels on the basis of a plurality of areas, into which a brain area, corresponding to one sensory area among the five senses, may be divided. For example, the acquisition unit 101 may separately acquire information about the activity level of an area, reacting to the movement of an object, within the visual area 91 and information about the activity level of another area, reacting to a color, within the visual area 91.

The reference value(s) stored in the storage unit (reference value storage unit) 14 does/do not have to be the value(s) set, based on the activity levels of the plurality of sensory areas 91-95 as acquired by the acquisition unit 101 when the subject is not exposed to any of the multiple types of stimuli. For example, the reference value(s) may be default value(s) which is/are stored in the storage unit 14 in advance.

The psychological condition estimation system 1 does not have to include the reference value storage unit 14. For example, the estimation unit (first estimation unit) 102 may use the activity level (activity level itself), acquired by the acquisition unit 101 while the estimation unit 102 is operating in the second mode, as the attention level. In that case, the estimation unit (first estimation unit) 102 estimates a sense with the highest attention level (i.e., activity level) of the corresponding sensory area, out of the plurality of types of senses, to be the sense that is highly related to the subject's psychological condition.

The estimation unit (first estimation unit) 102 does not have to be configured to estimate a sense with the highest attention level, out of the plurality of types of senses corresponding respectively to the plurality of sensory areas 91-95, to be the sense highly related to the subject's psychological condition. The estimation unit (first estimation unit) 102 may estimate, for example, by comparing each of the attention levels with respect to the plurality of sensory areas 91-95 with a threshold value, a sense corresponding to a sensory area associated with an attention level greater than the threshold value, to be the sense highly related to the subject's psychological condition. In that case, two or more senses may be estimated to be the senses that are highly related to the subject's psychological condition. The threshold values may be different from each other with respect to the attention levels for the plurality of sensory areas 91-95.

The reference value(s) may be obtained based on information about the activity levels, which are measured when the subject is spending a daily life, of the plurality of sensory areas 91-95.

The brain activity measuring unit (first measuring unit) 21 is not limited to the NIRS encephalometer but may be any other suitable device such as an MM (Magnetic Resonance Imaging) scanner or an electroencephalograph used for measuring electroencephalograms (such as gamma waves).

As the stimulus giving apparatus 4, existent equipment may also be used. For example, the control system 100 may use devices such as the lighting device and the air conditioner, which are provided for a building in advance, as the stimulus giving apparatus 4.

(5) Recapitulation

The embodiments and their variations described above may be specific implementations of the following aspects of the present disclosure.

A psychological condition estimation system (1) according to a first aspect includes an acquisition unit (101) and an estimation unit (102). The acquisition unit (101) acquires information about respective activity levels of a plurality of sensory areas (91-95) of a subject's brain (90). The estimation unit (102) estimates a sense, which is highly related to the subject's psychological condition, out of a plurality of types of senses corresponding respectively to the plurality of sensory areas (91-95), based on the information, acquired by the acquisition unit (101), about the activity levels of the plurality of sensory areas (91-95) when the subject is exposed to multiple types of stimuli.

According to this aspect, the psychological condition estimation system (1) may be used for determining a constituent factor of the subject's psychological condition.

In a psychological condition estimation system (1) according to a second aspect, which may be implemented in conjunction with the first aspect, the estimation unit (102) estimates a sense, of which a corresponding sensory area has a higher activity level than any other one of the plurality of sensory areas does, out of the plurality of types of senses, to be the sense highly related to the subject's psychological condition.

According to this aspect, the psychological condition estimation system (1) may be used for determining a constituent factor of the subject's psychological condition.

A psychological condition estimation system (1) according to a third aspect, which may be implemented in conjunction with the first aspect, further includes a reference value storage unit (14). The reference value storage unit (14) stores a plurality of reference values having one-to-one correspondence to the activity levels of the plurality of sensory areas (91-95). The estimation unit (102) estimates a sense, of which a corresponding sensory area has an activity level having a greater difference from a corresponding reference value than any other one of the plurality of sensory areas does, out of the plurality of types of senses, to be the sense highly related to the subject's psychological condition.

According to this aspect, the sense highly related to the subject's psychological condition may be estimated based on the reference values.

A psychological condition estimation system (1) according to a fourth aspect, which may be implemented in conjunction with the third aspect, further includes a reference value setting unit (103). The reference value setting unit (103) sets the plurality of reference values, based on the activity levels of the plurality of sensory areas (91-95) as acquired by the acquisition unit (101) when the subject is not exposed to any of the multiple types of stimuli.

According to this aspect, the sense highly related to the subject's psychological condition may be estimated by reference to the reference values which are set based on the activity levels of the plurality of sensory areas (91-95) when the subject is not exposed to any of the multiple types of stimuli.

In a psychological condition estimation system (1) according to a fifth aspect, which may be implemented in conjunction with any one of the first to fourth aspects, the estimation unit (102) serves as a first estimation unit. The psychological condition estimation system (1) further includes a second estimation unit (104). The second estimation (104) unit estimates the subject's psychological condition by using, as indices, the subject's level of valence and the subject's level of arousal.

According to this aspect, the first estimation unit (102) may estimate the sense highly related to the subject's psychological condition that has been estimated by the second estimation (104) unit.

In a psychological condition estimation system (1) according to a sixth aspect, which may be implemented in conjunction with any one of the first to fifth aspects, the plurality of types of senses include at least two senses selected from the group consisting of a visual sense, an auditory sense, an olfactory sense, a somatic sensation, and a gustatory sense.

According to this aspect, the psychological condition estimation system (1) may be used for determining a constituent factor of the subject's psychological condition.

A psychological condition estimation method according to a seventh aspect includes an acquisition step and an estimation step. The acquisition step includes acquiring information about respective activity levels of a plurality of sensory areas (91-95) of a subject's brain. The estimation step includes estimating a sense, which is highly related to the subject's psychological condition, out of a plurality of types of senses corresponding respectively to the plurality of sensory areas (91-95), based on the information about the activity levels of the plurality of sensory areas (91-95) as acquired when the subject is exposed to multiple types of stimuli.

According to this aspect, the psychological condition estimation method may be used for determining a constituent factor of the subject's psychological condition.

A program according to an eighth aspect is designed to cause one or more processors to perform the psychological condition estimation method according to the seventh aspect.

According to this aspect, the program designed to carry out the psychological condition estimation method may be used for determining a constituent factor of the subject's psychological condition.

A method for generating an estimation model according to a ninth aspect is used in the estimation unit (102) of the psychological condition estimation system (1) according to any one of the first to sixth aspects. The method for generating an estimation model includes an acquisition step and a model generating step. The acquisition step includes acquiring, when a subject is exposed to multiple types of stimuli, information about respective activity levels of a plurality of sensory areas (91-95) of a subject's brain (90). The model generating step includes generating the estimation model based on input data and output data by machine learning using, as the input data, information about respective activity levels of the plurality of sensory areas (91-95), and also using, as the output data, the sense highly related to the subject's psychological condition.

REFERENCE SIGNS LIST

1 Psychological Condition Estimation System
101 Acquisition Unit
102 Estimation Unit (First Estimation Unit)
103 Reference Value Setting Unit
104 Second Estimation Unit
14 Reference Value Storage Unit
90 Brain
91-95 Sensory Area

The invention claimed is:

1. A stimulus control system comprising:
an acquisition unit configured to acquire information about respective activity levels of a plurality of sensory areas of a subject's brain, including a visual area, an auditory area, an olfactory area, a somatosensory area, and a gustatory area;
a first estimation unit configured to estimate a specific sense, which is related to a subject's psychological condition, out of a plurality of types of senses including a visual sense, an auditory sense, an olfactory sense, a somatic sensation and a gustatory sense, the first estimation unit being configured to estimate the specific sense based on the information, acquired by the acquisition unit, about the activity levels of the plurality of sensory areas when the subject is exposed to multiple types of stimuli;
a second estimation unit configured to estimate the subject's psychological condition by using, as indices, a level of valence of the subject and a level of arousal of the subject;
a controller configured to control a stimulus giving apparatus based on the information about the respective activity levels of the plurality of sensory area, the stimulus giving apparatus being configured to adjust an intensity of at least one type of stimuli applied to the subject; and
an operating unit configured to receive an operation indicating a desired psychological condition which the subject wants to achieve, wherein
the stimulus control system is configured to estimate that a stimulus to the specific sense, which is at least one of the visual sense, the auditory sense, the olfactory sense, the somatic sensation and the gustatory sense and is estimated to be related to the subject's psychological condition by the first estimation unit, is a constituent factor of the subject's psychological condition estimated by the second estimation unit, and
the controller is configured to, when finding that the subject's psychological condition estimated by the second estimation unit is different from the desired psychological condition, control the stimulus giving apparatus such that the subject's psychological condition approaches the desired psychological condition by increasing or reducing the intensity of the stimulus to the specific sense which is estimated to be related to the subject's psychological condition by the first estimation unit.

2. The stimulus control system of claim 1, wherein
the first estimation unit is configured to estimate a sense, of which a corresponding sensory area has a higher activity level than any other one of the plurality of sensory areas does, out of the plurality of types of senses, to be the specific sense related to the subject's psychological condition.

3. The stimulus control system of claim 1, further comprising a reference value storage unit configured to store a plurality of reference values having one-to-one correspondence to the activity levels of the plurality of sensory areas, wherein
the first estimation unit is configured to estimate a sense, of which a corresponding sensory area has an activity level having a greater difference from a corresponding reference value than any other one of the plurality of sensory areas does, out of the plurality of types of senses, to be the specific sense related to the subject's psychological condition.

4. The stimulus control system of claim 3, further comprising a reference value setting unit configured to set the plurality of reference values, based on the activity levels of the plurality of sensory areas as acquired by the acquisition unit when the subject is not exposed to any of the multiple types of stimuli.

5. A stimulus control method comprising:
an acquisition step including acquiring information about respective activity levels of a plurality of sensory areas of a subject's brain, including a visual area, an auditory area, an olfactory area, a somatosensory area, and a gustatory area;
a first estimation step including estimating a specific sense, which is related to a subject's psychological condition, out of a plurality of types of senses including a visual sense, an auditory sense, an olfactory sense, a somatic sensation and a gustatory sense, the first estimation step including estimating the sense based on the information, acquired in the acquisition step, about the activity levels of the plurality of sensory areas as acquired when the subject is exposed to multiple types of stimuli;
a second estimation step including estimating the subject's psychological condition by using, as indices, a level of valence of the subject and a level of arousal of the subject;
a controlling step including controlling a stimulus giving apparatus based on the information about the respective activity levels of the plurality of sensory areas, the stimulus giving apparatus being configured to adjust an intensity of at least one type of stimuli applied to the subject; and
an operating step including receiving an operation indicating a desired psychological condition which the subject wants to achieve, wherein
the stimulus control method includes estimating that a stimulus to the specific sense, which is at least one of the visual sense, the auditory sense, the olfactory sense, the somatic sensation and the gustatory sense and is estimated to be related to the subject's psychological condition in the first estimation step, is a constituent factor of the subject's psychological condition estimated in the second estimation step, and
the controlling step includes, when finding that the subject's psychological condition estimated in the second estimation step is different from the desired psychological condition, controlling the stimulus giving apparatus such that the subject's psychological condition approaches the desired psychological condition by increasing or reducing the intensity of the stimulus to the specific sense which is estimated to be related to the subject's psychological condition in the first estimation step.

6. A non-transitory computer readable medium having stored thereon a program designed to cause one or more processors to perform the psychological condition estimation method of claim 5.

7. A method for generating an estimation model for use in the first estimation unit of the psychological condition estimation system of claim 1, the method comprising:
an acquisition step including acquiring, when the subject is exposed to the multiple types of stimuli, information about the respective activity levels of the plurality of sensory areas of the subject's brain; and
a model generating step including generating the estimation model based on input data and output data by machine learning using, as the input data, the information about the respective activity levels of the plurality of sensory areas, and also using, as the output data, the sense highly related to the subject's psychological condition.

8. The stimulus control system of claim 1, wherein the stimulus giving apparatus includes at least one selected from a group consisting of a lighting device, a display device, a sound emitter, a blower, an air conditioner, a taste stimulator configured to give a stimulus to the subject's gustatory sense, or an air purifier.

9. The stimulus control system of claim 8, wherein
the controller is configured to:
when finding that an activity level of any one of the plurality of sensory areas exceeds a predetermined threshold, control the stimulus giving apparatus such that the activity level of the any one of the plurality of sensory areas that has been found to exceed the predetermined threshold is decreased; or
when finding that an activity level of any one of the plurality of sensory areas is lower than the predetermined threshold, control the stimulus giving apparatus such that the activity level of the any one of the plurality of sensory areas that has been found to be lower than the predetermined threshold is increased.

* * * * *